United States Patent [19]
Ohemeng et al.

[11] Patent Number: 5,942,532
[45] Date of Patent: Aug. 24, 1999

[54] 2-SUBSTITUTED PHENYL-BENZIMIDAZOLE ANTIBACTERIAL AGENTS

[75] Inventors: Kwasi Adomako Ohemeng, Flemington, N.J.; Van Nhatton Nguyen, Easton, Pa.

[73] Assignee: Ortho Pharmaceutical Corporation, Raritan, N.J.

[21] Appl. No.: 08/924,558

[22] Filed: Sep. 5, 1997

[51] Int. Cl.⁶ ........................ A61K 31/34; A61K 31/415; C07D 233/06; C07D 207/06
[52] U.S. Cl. ........................ 514/396; 514/218; 514/241; 514/242; 514/253; 514/256; 514/322; 514/339; 514/341; 514/365; 514/372; 514/383; 514/397; 514/399; 514/409; 514/411; 514/422; 514/454; 514/456; 540/553; 540/603; 544/180; 544/333; 544/366; 546/199; 546/256; 546/273.4; 548/202; 548/205; 548/214; 548/255; 548/411; 548/440; 548/518; 549/406; 549/414; 549/460
[58] Field of Search ................................... 514/396, 399; 548/354.1

[56] References Cited

U.S. PATENT DOCUMENTS 4,982,112  1/1991  Okazaki et al. ........................ 307/425

FOREIGN PATENT DOCUMENTS

| 0 148 431 | 8/1984 | European Pat. Off. . |
| 0 353 606 | 7/1989 | European Pat. Off. . |
| 0 511 187 A1 | 3/1992 | France . |
| 30 7 188 A1 | 2/1980 | Germany . |
| 2-306916 | of 1990 | Japan . |
| 2 125 790 | 8/1982 | United Kingdom . |
| WO96/06831 | 3/1996 | WIPO . |

OTHER PUBLICATIONS

Aunê et al., "Antifungal and Antibacterial Activities of Diarylamine Derivatives," *Antimicrobial Agents and Chemotherapy* (Aug. 1980), vol. 18(2) pp. 231–239.

Ertepinar, H, Gok, Y, Geban O.. 1995, A QSAR Study of the Biological Activities of Some Benzimidazoles and Imidazopyridines Against Bacilus Subtilis,Jur. J. Med Chem 30, 171–175.

Coburn, R., Clark, Michael T. Evans, Richard T,., Genco, Robert J., (1987) Substituted 2–(2–Hydroxyphenyl) Benzimidazoles as Potential Agents for the Control of Periodontal Diseases, J. Med Chem.,, 205–208.

Dharti, Joshi, Haresh, Oza, Parekh, H., (1997), Synthesis of Some Novel 1.3.4–Oxadiazoles and 5–Oxo–Imidazolines as Potent Biologically Active Agents, vol. 3,. No.2.

Chem. Abstracts 89:101871C(1978) Substituted Benimidazole Fungicides.

Scifinder Abstract, Shanghai Insti. Pharm. Ind, Yiyao Gongye (1985) 16(a): 394–9.

Chem. Abstracts, 77:153703w (1972) Polyamide Compositions.

Derwent Publication Abstract 52259R–BCD, CH—490011–R CIBA AG (1968).

Derwent Publication Abstract 77356T–BC, DT–2122208–Farbwerke Hoechst (1971).

Derwent Publication Abstract 25469C/15. DT2839989 (1978).

Derwent Publication Abstract 95–149092/20, ES2068115 (1993).

International Journal of Pharmaceutics, 98 (1993) 1–8, QSARS of Some Novel Antibacterial Benzimidazoles, Benzimidazoles, Bensoaxazoles, and Oxazolopyridines Against an Entric Gam–Negative Rod; K.Penumoniae.

J. Med Chem (1995) 30.171–175 Elsevier Paris, A QSAR Study of The Biological Activities of Some Benzimidazoles and Imidazopyridines against Bacillus Subtilis.

Journal of Medicinal Chemistry, 1978, vol. 21, No. 7, Diarylamidine Derivatives With One or Both of The Aryl Moieties Consisting of an Indole or Indole–Like Ring. Inhibitors of Arginine–Specific Esteroproteases.

Jouranal of Mecicinal Chemistry 1993 36, 1746–1753, Structure DNA Minor Groove Binding, and BASE Pair Specificity of Alkyl–and Aryl–Linked Bis(Amidinobenzimidazoles) and Bis(Amidinoindoles).

*Primary Examiner*—Johann Richter
*Assistant Examiner*—Jane C. Oswecki
*Attorney, Agent, or Firm*—Kenneth J. Dow

[57] ABSTRACT

The invention relates to benzimidazole antibacterial compounds of the Formula I:

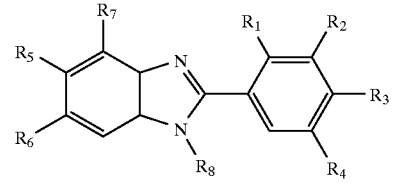

Formula I as described herein, pharmaceutical compositions containing the compounds, and methods for their production and use. These compounds are effective in inhibiting the action of a bacterial histidine protein kinase and are useful as anti-infective agents against a variety of bacterial organisms, including organisms which are resistant to other known antibiotics.

15 Claims, No Drawings

2-SUBSTITUTED PHENYL-BENZIMIDAZOLE ANTIBACTERIAL AGENTS

FIELD OF THE INVENTION

The invention relates to benzimidazole antibacterial compounds, pharmaceutical compositions containing the compounds, and methods for their production and use. These compounds are effective in inhibiting the action of a bacterial histidine protein kinase and are useful as anti-infective agents against a variety of bacterial organisms, including organisms which are resistant to other known antibiotics.

BACKGROUND OF THE INVENTION

It is well established that prokaryotes regulate the transcription of many of their genes in response to changes in the organisms' environment (J. B. Stock, A. M. Stock, and J. M. Mottonen, *Nature,* 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, *Science,* 243, 1059 (1989). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processes is expected to lead to reduced virulence, a slowing or halting of bacterial growth and reproduction, and even to bacterial cell death if vital functions are interrupted.

For example, it has been shown that Salmonella species express certain proteins, under regulatory control and in response to the presence of epithelial cells, which enable them to adhere to and invade intestinal epithelial cells. Bacteria that are unable to synthesize these proteins are avirulent: they cannot cause infection in mice (B. B. Finlay, F. Heffron, S. Falkow, *Science,* 243, 940–943 (1989)). A similar effect would be expected if the genes coding for these proteins were intact, but remained unexpressed.

To accomplish adaptive responses to the environment, bacteria rely on phosphorelay mechanisms, referred to in the art as a "two-component switches." These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Most of these HPK enzymes are sensor molecules, and respond to stimulation by specific environmental signals by transferring phosphate from ATP to a histidine residue of the HPK protein. Some HPK enzymes are stimulated by the presence of acceptor proteins (described below), the concentration of which are modulated by environmental signals. In either case, this auto-phosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Mammalian cells do not, or at least are not presently known to, utilize HPK-driven phosphorelay systems for gene regulation. Thus, compounds which selectively inhibit either the autophosphorylation of the HPK protein, or the phosphotransfer step(s), or both, would not be expected to have undesirable effects on the host organism, and are promising candidates for antiinfective drugs. The emergence of drug-resistant pathogenic organisms that are resistant to one or more of the currently available drugs has created a need for novel antibiotics, that act by mechanisms unrelated to those of currently available agents, and inhibitors of HPK would fill this need. The presence of multiple HPK-driven systems (over fifty are currently known) in bacteria gives HPK inhibitors a potential advantage over current antibiotics, in that mutations of a single HPK enzyme are unlikely to confer drug resistance to an organism.

Recently, workers in this field reported a method for detecting bacterial "virulence" genes that are selectively expressed when bacteria infect a host (M. J. Mahan, J. M. Slauch, and J. J. Mekalanos, *Science,* 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in *Pseudomonas aeruginosa* in an in vitro system (S. Roychoudhury et al., *Proc. Nat. Acad. Sci.,* 90, 965–969 (1993)), but no anti-bacterial activity of the compounds was reported.

SUMMARY OF THE INVENTION

The invention relates to compounds of the Formula I:

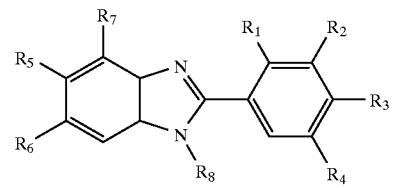

Formula I wherein:

$R_1$ is selected from H, OH, $(C_1-C_6)$alkoxy, and —O$(C_1-C_3)$COOH;

$R_2$, $R_3$ and $R_4$ are independently selected from H, OH, $(C_1-C_{10})$alkyl (branched or unbranched), $(C_1-C_{10})$ alkoxy, —O$(C_1-C_3)$COOH, —O$(C_1-C_6)$alkylphenyl, —OCH$_2$(4-NO$_2$phenyl), CF$_3$, halo, phenyl, substituted phenyl (wherein the substituents are selected from halogen, $(C_1-C_6)$alkoxy, nitro, NH$_2$, and $(C_1-C_6)$ alkyl), —$(C_1-C_6)$alkylphenyl, nitro, —O(CH$_2$)$_q$N$((C_1-C_6)$alkyl)$_2$ wherein q is 1–3, —NR$_{17}$R$_{18}$, 2-thiazole optionally substituted by a $(C_1-C_6)$ alkyl group, —CH=CH-phenyl, pyridinyl, piperidinyl, —N-phenyl substituted piperidine, —O-piperazine, pyrrolinyl, and a moiety of the formula:

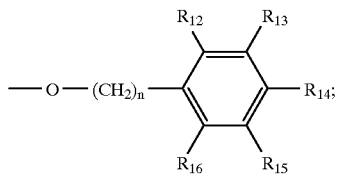

wherein n is an integer from 0–2;

$R_{12}$, $R_{13}$, $R_{14}$, $R_{15}$ and $R_{16}$ are independently selected from H, nitro, halo, $CF_3$, $(C_1-C_6)$ alkyl, $(C_1-C_6)$ alkoxy, and amino, amidine, sulfonate, —C(O)O $(C_1-C_6)$alkyl, and carboxyl;

or $R_{13}$ and $R_{14}$ or $R_{14}$ and $R_{15}$ taken together form a fused 5 membered heterocyclic ring of the formula:

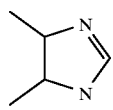

which may be optionally substituted wherein the substituent is selected from amino and methyl;

$R_{17}$ and $R_{18}$ are independently selected from H, benzyl, phenyl, $(C_1-C_6)$alkyl, $CH_2CN$, $CH_2CH_2CN$, or $R_{17}$ and $R_{18}$ taken together with the nitrogen to which they are attached form a 5–6 membered monocyclic heterocyclic ring optionally containing 1–2 additional nitrogen atoms;

or $R_2$ and $R_3$ or $R_3$ and $R_4$ taken together with the phenyl ring to which they are attached form a moiety selected from those of the formulae:

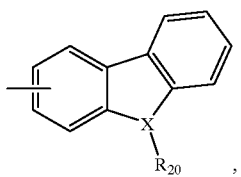

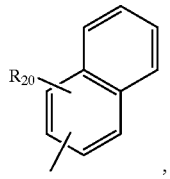

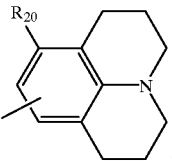

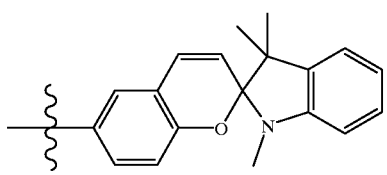

wherein X is CH, O or N and $R_{20}$ is $(C_1-C_3)$alkyl or OH;

$R_5$ is selected from H, amino and amidino;

$R_6$ is selected from nitro and moieties of the formula:

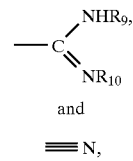

and

≡N, wherein:

$R_9$ is hydrogen and $R_{10}$ is selected from H or OH or $R_9$ and $R_{10}$ taken together form a 5, 6 or 7 membered monocyclic heterocyclic ring optionally containing 1 or 2 additional nitrogens and optionally substituted wherein the substituent is dimethyl, or $R_9$ and $R_{10}$ taken together form a bicyclic heterocyclic ring of the formula;

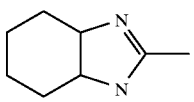

$R_7$ is selected from H, amino and nitro;

$R_8$ is selected from H and methyl;

and the pharmaceutically acceptable salts, esters and prodrug forms thereof.

The compounds of the present invention inhibit the autophosphorylation of bacterial histidine kinases; they also inhibit the transfer of phosphate from phosphorylated histidine kinases to the aspartyl residues of the phosphate acceptor proteins involved in regulation of bacterial gene expression. The compounds of the present invention have been found to inhibit the growth of bacteria by the standard method, measurement of minimum inhibitory concentrations (MIC values). The compounds are useful as bacteriostatic and bactericidal agents.

DETAILED DESCRIPTION OF THE INVENTION

As used herein, the term "alkyl" means branched or unbranched hydrocarbon chains, such as, for example, methyl, ethyl, n-propyl, iso-propyl, n-butyl, sec-butyl, tert-butyl, and the like. The alkyl group may be optionally substituted with one or more functional groups commonly attached to such chains, for example, hydroxy, halo, mercapto, thio, cyano, alkylthio, nitro, amino, alkoxy, amido, carboxyl, alkoxycarbonyl, amidino, guanidino and the like.

The term "alkoxy" means the group —OR, where R is an alkyl group as defined above, such as methoxy, ethoxy, n-propoxy, iso-propoxy, n-butoxy, sec-butoxy, iso-butoxy, tert-butoxy and the like.

The term "amino" includes primary, secondary and tertiary amines of the formula —NRR' where R and R' are independently hydrogen or alkyl as defined above.

The term "amido" means a group of the formula —C(O) NRR', where R and R' may independently be hydrogen or alkyl as defined above.

The term "prodrug" means an agent which is converted into the parent drug in vivo. Prodrugs may be used to deliver the drug in a manner that is easier or more efficiently delivered. For instance, a drug which is not orally bioavailable may be orally administered in a prodrug form which is orally available, or the prodrug form may be more soluble for administration intravenously.

Within the group of compounds defined by Formula I, certain subgroups of compounds are preferred. Broadly preferred are those compounds of Formula I wherein:

$R_1$ is selected from H, OH, $(C_1-C_6)$alkoxy, and —$O(C_1-C_3)$COOH;

$R_2$ is selected from H, $(C_1-C_{10})$alkyl (branched or unbranched), $(C_1-C_{10})$alkoxy; —$O(C_1-C_{10})$alkylphenyl, $CF_3$, halo, phenyl, nitro, pyridyl, and a moiety of the formula:

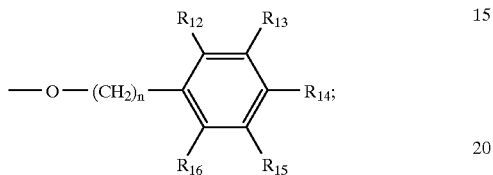

$R_3$ is selected from H, OH, $(C_1-C_{10})$alkyl (branched or unbranched), $(C_1-C_{10})$alkoxy, —$O(C_1-C_6)$alkylphenyl, —$OCH_2(4\text{-}NO_2\text{phenyl})$, $CF_3$, halo, phenyl, substituted phenyl (wherein the substituents are selected from halogen, $C_1-C_6$alkoxy, nitro, $NH_2$, and $(C_1-C_6)$alkyl), —$(C_1-C_6)$alkylphenyl, nitro, —$O(CH_2)_qN((C_1-C_6)$alkyl$)_2$ wherein q is 1–3, —$NR_{17}R_{18}$, 2-thiazole optionally substituted by a $C_1-C_6$ alkyl group, —CH=CH-phenyl, —N-phenyl substituted piperidine, —O-piperazine, pyrrolinyl, and a moiety of the formula:

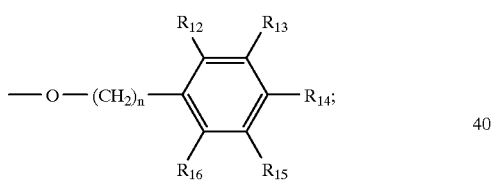

wherein $R_{17}$ and $R_{18}$ are independently selected from H, benzyl, phenyl, $(C_1-C_6)$alkyl, $CH_2CN$, $CH_2CH_2CN$, or $R_{17}$ and $R_{18}$ taken together with the nitrogen to which they are attached form a 5–6 membered monocyclic heterocyclic ring optionally containing 1–2 additional nitrogen atoms;

$R_4$ is selected from H, $(C_1-C_{10})$alkyl (branched or unbranched), $(C_1-C_{10})$alkoxy; —$O(C_1-C_6)$alkylphenyl, $CF_3$, halo, phenyl, nitro and a moiety of the formula:

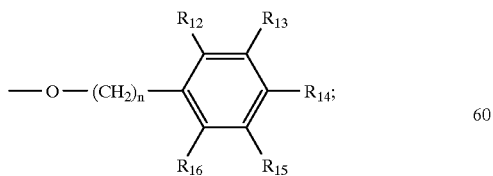

or $R_2$ and $R_3$ or $R_3$ and $R_4$ taken together with the phenyl ring to which they are attached form a moiety selected from those of the formulae:

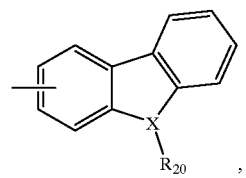

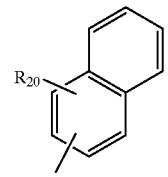

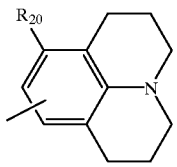

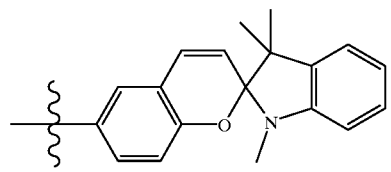

wherein X is CH, O or N and $R_{20}$ is $(C_1-C_3)$alkyl or OH;

$R_5$ is selected from H, amino and amidino;

$R_6$ is selected from nitro and moieties of the formula:

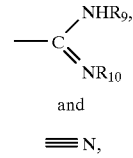

and

≡N, wherein:

$R_9$ is hydrogen and $R_{10}$ is selected from H or OH or $R_9$ and $R_{10}$ taken together form a 5, 6 or 7 membered monocyclic heterocyclic ring optionally containing 1 or 2 additional nitrogens and optionally substituted wherein the substituent is dimethyl, or $R_9$ and $R_{10}$ taken together form a bicyclic heterocyclic ring of the formula;

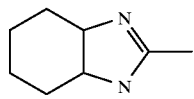

$R_7$ is selected from H, amino and nitro;
$R_8$ is selected from H and methyl;
$R_{12}$ is selected from H and nitro;
$R_{13}$ is selected from H, nitro, halo, $CF_3$, $(C_1-C_6)$ alkyl, $(C_1-C_6)$ alkoxy, and amino;
$R_{14}$ is selected from H, nitro, halo, $CF_3$, $(C_1-C_6)$ alkyl, $(C_1-C_6)$ alkoxy, amino, amidine, sulfonate, —C(O)O$(C_1-C_6)$alkyl, and carboxyl;
$R_{15}$ is selected from H, nitro, halo, $CF_3$, $(C_1-C_6)$ alkyl, $(C_1-C_6)$ alkoxy, and amino;

$R_{16}$ is selected from H and nitro;

or $R_{13}$ and $R_{14}$ or $R_{14}$ and $R_{15}$ taken together form a fused 5 membered heterocyclic ring of the formula:

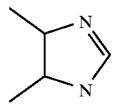

which may be optionally substituted wherein the substituent is selected from amino and methyl;

n is an integer from 0–2;

and the pharmaceutically acceptable salts, esters and prodrug forms thereof.

More particularly preferred are the compounds wherein $R_1$–$R_4$ are as described above;

$R_5$ is H;

$R_6$ is a moiety of the formula:

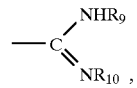

wherein:

$R_9$ is hydrogen and $R_{10}$ is selected from H or OH or $R_9$ and $R_{10}$ taken together form a 5, 6 or 7 membered monocyclic heterocyclic ring optionally containing 1 or 2 additional nitrogens and optionally substituted wherein the substituent is dimethyl, or $R_9$ and $R_{10}$ taken together form a bicyclic heterocyclic ring of the formula;

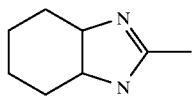

$R_7$ and $R_8$ are hydrogen and $R_{12}$ to $R_{16}$ are as described above;

and the pharmaceutically acceptable salts, esters and prodrug forms thereof.

Most preferred are the 5-amidino compounds of Formula I wherein:

$R_1$ is selected from H, OH, $(C_1-C_6)$alkoxy;

$R_2$ is selected from H, $(C_1-C_{10})$alkyl (branched or unbranched), $(C_1-C_6)$alkoxy; —O$(C_1-C_{10})$ alkylphenyl, $CF_3$, halo, phenyl, nitro and a moiety of the formula:

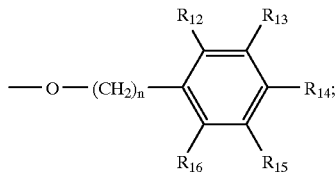

$R_3$ is selected from H, OH, $(C_1-C_{10})$alkyl (branched or unbranched), $(C_1-C_{10})$alkoxy, —O$(C_1-C_6)$ alkylphenyl, $CF_3$, halo, phenyl, substituted phenyl (wherein the substituents are selected from halogen, $(C_1-C_6)$alkoxy, nitro, $NH_2$, and $(C_1-C_6)$alkyl), —$(C_1-C_6)$ alkylphenyl and a moiety of the formula:

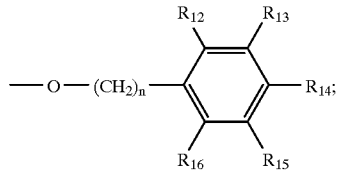

$R_4$ is selected from H, $(C_1-C_{10})$alkyl (branched or unbranched), and —OCH$_2$phenyl;

$R_5$ is H;

$R_6$ is amidine;

$R_7$ is H;

$R_8$ is H;

n is 0;

$R_{12}$ is H;

$R_{13}$ is selected from H, nitro, halo, $CF_3$, $C_1-C_6$) alkyl, $(C_1-C_6)$ alkoxy, and amino;

$R_{14}$ is selected from H, nitro, halo, $CF_3$, $(C_1-C_6)$ alkyl, $(C_1-C_6)$ alkoxy and amino;

$R_{15}$ is selected from H and $(C_1-C_6)$ alkoxy, and amino;

$R_{16}$ is H;

and the pharmaceutically acceptable salts, esters and prodrug forms thereof.

The compounds of the present invention may generally be prepared in accordance with the following schemes, but other synthetic pathways are possible and are within the scope of this invention.

The benzimidazole compounds of the present invention may be prepared in accordance with Scheme I by one of the following two routes: A) Cyclization of the appropriately substituted diaminophenyl compound with an appropriately substituted aldehyde [(as the bisulphite adduct) in accordance with the procedures disclosed by H. F. Ridley, R. G. W. Spickett and G. M. Timmis; J. Heterocycl Chem 2, 455, 1965] or B) Cyclization of the diaminophenyl compound with the appropriately substituted imidate to give the benzimidazole.

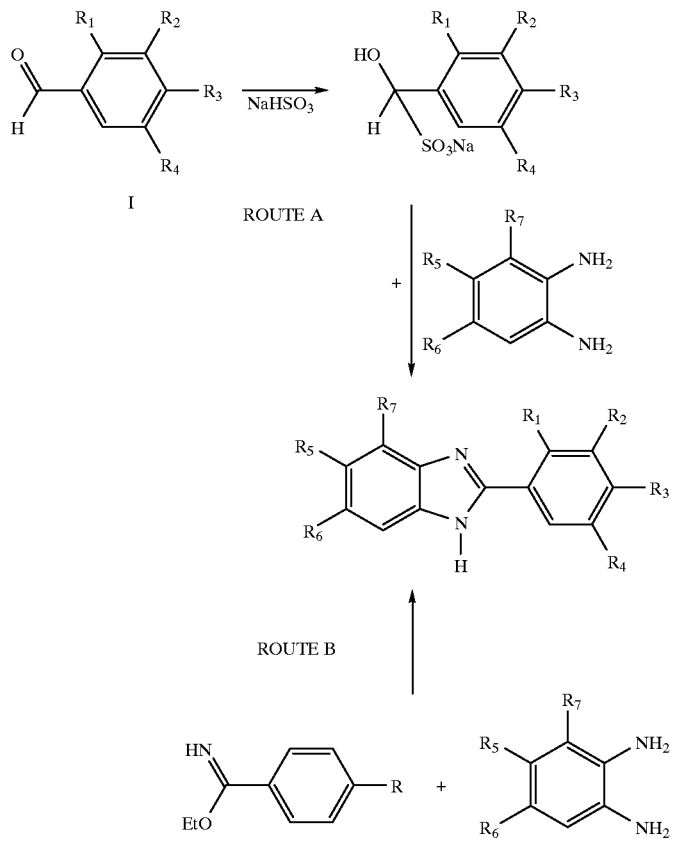

Scheme I

All the amidino benzimidazoles may be synthesized by these methods in accordance with Scheme II by cyclization of the appropriately substituted aldehyde [(as the bisulphite adduct with diaminobenzamidine] or cyclization of diaminobenzonitrile with the appropriate aldehyde (as the bisulphite adduct) or imidate to give an intermediate nitrile which is then converted to the final product by the Pinner's reaction, i.e. by treating the intermediate nitrile with HCl gas in ethanol to form the imidate followed by reaction with ammonia in ethanol to form the amidine.

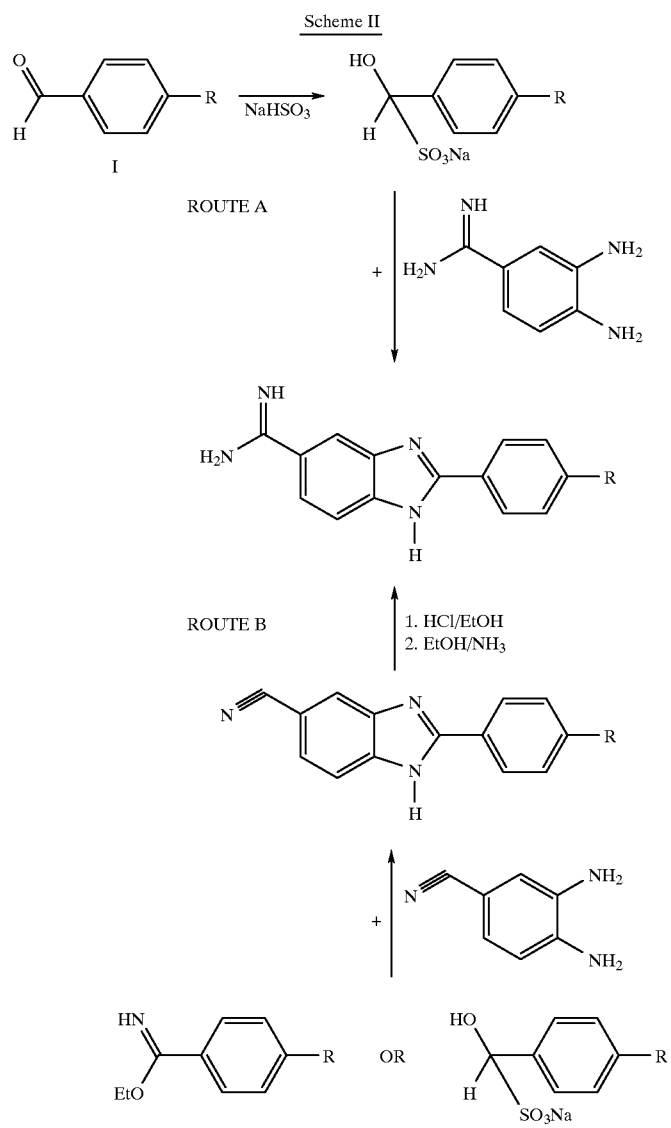

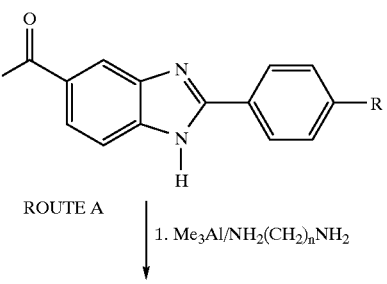

The cyclic amidines (imidazolines etc.) may be synthesized by two routes (Scheme III); (A) reaction of the appropriately substituted esters with a diamine in the presence of trimethylaluminium (G. Neef, U. Eder and G. Sauer; J. Org. Chem. 46, 2824–2826) and (B) reaction of the appropriately substituted nitrile with ethanolic HCl to give the imidate followed by reaction with the appropriate diamine.

-continued

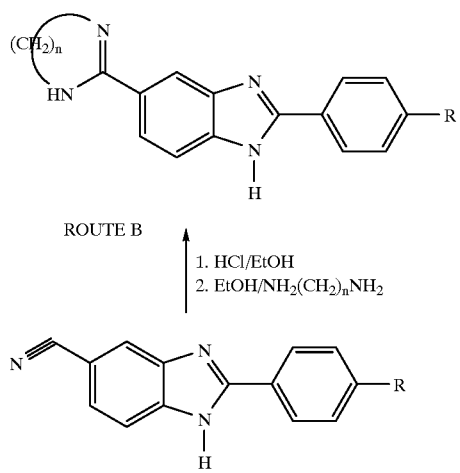

ROUTE B

1. HCl/EtOH
2. EtOH/NH$_2$(CH$_2$)$_n$NH$_2$

The aldehyde I starting materials may be obtained commercially or may be synthesized by methods known in the art. For example, the phenoxy derivatives where R$_2$ or R$_3$ are moieties of the formula:

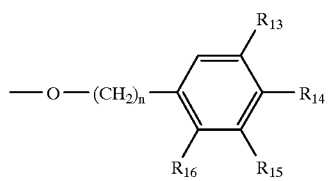

may be synthesized in one of the following routes (Scheme IV): A.) Reduction of the corresponding commercially available nitrile II to the aldehyde with diisobutylaluminum hydride (A. E. G. Miller, J. W. Biss, and L. H. Schwartzman; J. O. C. 24, 627, 1959), or B.) Nucleophilic displacement reaction of the appropriately substituted halo-aromatic aldehyde or halo-aromatic nitrile with the corresponding phenols. In the second instance the nitriles obtained may either be converted to the final products or reduced with diisobutylaluminum hydride to give the aldehydes.

Scheme IV

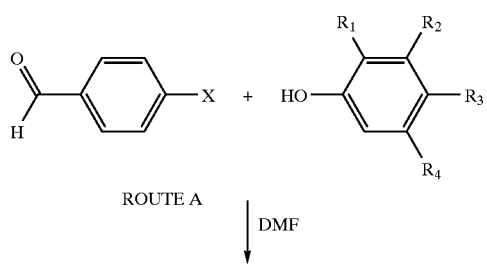

ROUTE A

DMF

-continued

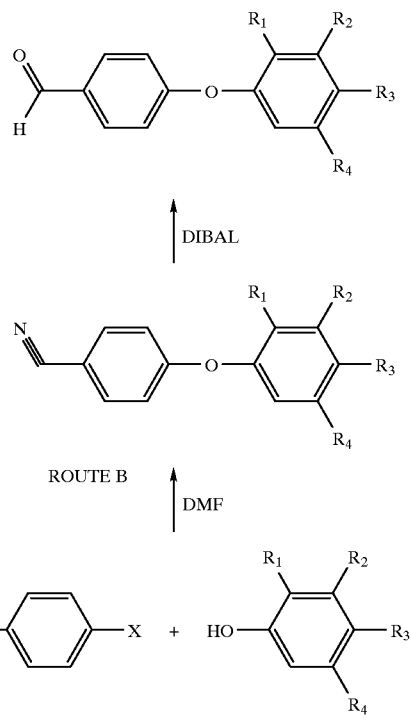

Similarly, the piperazine derivatives may be synthesized by nucleophilic displacement reaction of the appropriately substituted halo-aromatic aldehyde or halo-aromatic nitrile with the corresponding piperazine as in Scheme V.

Scheme V

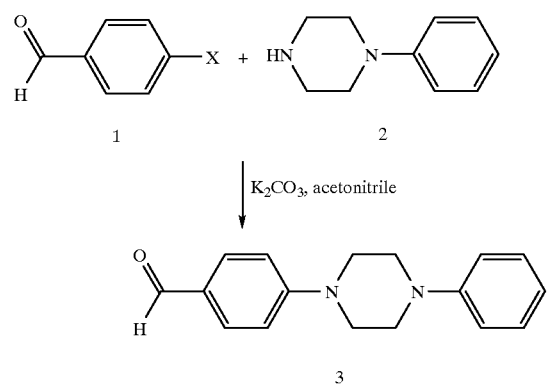

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula I it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of known principles. Enantiomers may be separated from each other by the selective crystallization of the diasteromeric salts with optically active bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, $Ca(OH)_2$, $Al(OH)_3$, piperidine, morpholine, ethylamine, triethylamine and the like.

The pharmaceutically acceptable esters of the present invention are such as would be readily apparent to those skilled in the art particularly those biolabile esters which are hydrolyzed under physiological conditions, for example alkoxyalkyl, cycloalkoxyalkyl, alkenyloxyalkyl, aryloxyalkyl, alkoxyaryl, alkylthioalkyl, cycloalkylthioalkyl, alkenylthioalkyl or alkylthioaryl esters. Particular examples are the pivaloyloxymethyl, acetoxymethyl, phthalidyl, indanyl, and methoxymethyl esters.

Also included within the scope of the invention are the hydrated forms of the compounds which contain various amounts of water, for instance, the hydrate, hemihydrate and sesquihydrate forms.

The ability of bacteria to quickly respond to changes in the environment is of utmost importance for their survival. Bacteria are capable of rapidly responding and adapting to such diverse stimuli as changes in nutrients, osmolarity, temperature, light, or host environment. These responses may be transient, such as those required for changes in motility or for entry into a host cell. Alternatively, the responses may require major shifts in gene expression and cell morphology, such as those required for sporulation, or for survival within a macrophage. The mechanism by which bacteria are able to sense cues from the physical environment (or from within the cytoplasm) and process these signals into appropriate responses often involves the so-called "two-component" systems.

As stated above, the antibacterial activity of the compounds of the present invention is based on the inhibition of this "two-component switch" system. All bacteria use this mechanism to control various adaptive/virulence factors to facilitate establishment of a bacterial population in the environment (for example, a bacterial infection in a host). The system invariably consists of a sensor which either activates a kinase or is a part of the kinase, and which upon stimulation, autophosphorylates. This phosphorylated species is a highly active phosphodonor which immediately transfers its phosphate to a "regulatory" component, which in turn initiates the biological response such a transcription or further phosphotransfer in a cascade which eventually ends in regulation of bacterial gene expression. Although each of the kinases and response regulators has a unique sequence (in fact, even functionally identical proteins have slightly different sequences in different species) they share a homologous biochemical mechanism and they share significant homology in the active site.

Accordingly, the present invention provides compounds which exhibit antibiotic activity by inhibiting the autophosphorylation of these bacterial histidine kinases. They also inhibit the transfer of phosphate from phosphorylated histidine kinases to the aspartyl residues of the phosphate acceptor proteins involved in regulation of bacterial gene expression.

The compounds of the present invention have antibacterial activity as determined by the following tests. First, the compounds were tested for their activity in inhibiting the autophosphorylation of Kinase A and the transphosphorylation of Spo0F, two proteins involved in one of the above described signal transduction systems controlling gene expression in bacteria. Representative compounds were then tested for antibacterial activity against selected organisms by the standard MIC method. The results are set forth below.

Tables 1–6 list examples of compounds of the invention, along with their $IC_{50}$ values in the HPK in vitro assay described below, and MIC value ranges for the selected microorganisms identified below. These examples are merely illustrative of the invention, and are not intended to limit the scope of the claims in any way.

TABLE 1

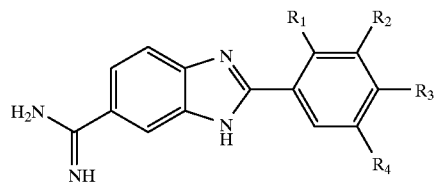

| Example | $R_1$ | $R_2$ | $R_3$ | $R_4$ | $IC_{50}$ |
|---|---|---|---|---|---|
| 2 | H | H | Ph | H | 86 |
| 3 | H | H | $CF_3$ | H | 169 |
| 4 | H | H | i-Propyl | H | 219 |
| 5 | H | H | $N(Ph)_2$ | H | 17.4 |
| 6 | H | $OCH_2Ph$ | H | $OCH_2Ph$ | 15.9 |
| 7 | H | $CF_3$ | H | $CF_3$ | 30.8 |
| 8 | H | H | $C(CH_3)_2CH_2CH_3$ | H | 37.6 |
| 9 | H | t-Butyl | OH | t-Butyl | 75.9 |
| 10 | H | H | t-Butyl | H | 70.6 |
| 11 | H | H | $OCH_2(4-NO_2Ph)$ | H | 19.4 |

TABLE 1-continued

Structure: benzimidazole with H₂N-C(=NH)- group and 2-aryl substituent bearing R₁, R₂, R₃, R₄

| Example | R₁ | R₂ | R₃ | R₄ | IC$_{50}$ |
|---|---|---|---|---|---|
| 12 | H | OC$_{10}$H$_{21}$ | OC$_{10}$H$_{21}$ | H | 8.3 |
| 13 | H | H | CHCHPh | H | 21.5 |
| 14 | H | H | N(C$_4$H$_9$)$_2$ | H | 35.5 |
| 15 | H | H | OCH$_2$Ph | H | 60.8 |
| 16 | H | OCH$_2$Ph | OCH$_2$Ph | H | 50.7 |
| 17 | H | H | F | H | 480 |
| 18 | H | I | OH | I | 254 |
| 19 | H | Cl | H | Cl | 100 |
| 20 | H | t-Butyl | H | t-Butyl | 19 |
| 21 | H | Ph | H | Ph | 31 |
| 22 | H | H | NHCH$_2$Ph | H | 222 |
| 23 | H | H | OH | t-Butyl | 22 |
| 24 | H | H | Pyrrolinyl | H | 93 |
| 25 | H | H | N(CH$_2$CH$_2$CN)$_2$ | H | 35.6 |
| 26 | H | H | N(CH$_2$Ph)$_2$ | H | 17 |
| 27 | OH | H | H | H | 465 |
| 28 | OCH$_3$ | H | OCH$_3$ | Br | 66 |
| 29 | OCH$_3$ | t-Butyl | H | t-Butyl | 76 |
| 30 | OH | t-Butyl | H | t-Butyl | 8.5 |
| 31 | OH | I | H | I | 30.8 |
| 32 | OH | Br | H | Br | 51.1 |
| 33 | OH | NO$_2$ | H | NO$_2$ | 74.7 |
| 34 | OH | t-Butyl | H | H | 4 |
| 35 | OH | H | H | t-Butyl | 64 |
| 36 | OH | Cl | H | Cl | 155 |
| 37 | OH | Br | H | OCH$_3$ | 171 |
| 38 | OH | H | N(CH$_2$CH$_3$)$_2$ | H | 51 |
| 39 | OH | Ph | H | Ph | 23 |
| 40 | OH | Br | H | NO$_2$ | 199 |
| 41 | H | Pyridine | H | H | 271 |
| 42 | OCH$_2$COOH | t-Butyl | H | t-Butyl | 199 |
| 43 | H | H | 4-t-butyl-thiazol-2-yl | H | 40.2 |
| 44 | H | H | 9-oxo-fluorenyl | H | 24.9 |
| 45 | H | H | 2,6-dinitro-4-(trifluoromethyl)phenoxy | H | 28 |

TABLE 3

| Example | R₁ | R₂ | R₃ | IC$_{50}$ (μM) |
|---|---|---|---|---|
| 63 | H | H | H | 53 |
| 64 | CF₃ | H | H | 48 |
| 65 | H | CH₃ | H | 33 |
| 66 | Cl | H | Cl | 32 |
| 67 | Cl | Cl | H | 32 |
| 68 | H | t-Butyl | H | 31.6 |
| 69 | H | Cl | H | 28 |
| 70 | H | OCH₃ | H | 69.2 |

TABLE 4

| Example | R | IC$_{50}$ (μM) |
|---|---|---|
| 71 | dibenzofuran-2-yl | 17.3 |
| 72 | fluoren-2-yl | 64.3 |
| 73 | 9-ethylcarbazol-3-yl | 22.0 |
| 74 | naphthalen-2-yl | 120 |
| 75 | 1-hydroxynaphthalen-2-yl | 127 |
| 76 | julolidin-yl | 85 |
| 77 | hydroxy-julolidin-yl | 18.5 |
| 78 | spiro[chromene-indoline] | 114 |

TABLE 5

[Structure: 6-R1-substituted benzimidazole with N-R2 and 2-(4-R3-phenyl) group]

| Example | R1 | R2 | R3 | IC$_{50}$ |
|---|---|---|---|---|
| 79 | H | H | O-C6H4-C(=NH)NH2 (4-amidinophenoxy) | 241 |
| 80 | H2N-C(=NH)- (acetamidine) | H | O-(1H-benzimidazol-5-yl) | 94 |
| 81 | H2N-C(=NH)- (acetamidine) | H | N-piperazinyl-N'-Ph | 26 |
| 82 | H2N-C(=NH)- (acetamidine) | -CH2-C(=NH)NH2 | N(Ph)2 | 22 |

TABLE 6

[Structure: 6-R-substituted 1H-benzimidazole with 2-(2-R1, 3-R2, 4-R3, 5-R4-phenyl) group]

| Example | R | R1 | R2 | R3 | R4 | IC$_{50}$ |
|---|---|---|---|---|---|---|
| 83 | 2-(4,5-dihydro-1H-imidazolyl) | H | H | OPh | H | 112.4 |
| 84 | 2-(1H-benzimidazolyl) | H | H | OPh | H | 32.3 |
| 85 | 2-(4,5-dihydro-1H-imidazolyl) | OH | t-butyl | H | t-butyl | 4 |
| 86 | N-propyl acetimidoyl | OH | t-butyl | H | t-butyl | 32 |

The protocol for the above referenced assay is as follows.
Autophosphorylation of Kinase A and Transphosphorylation of Spo0F Assay To study the effect of the compounds of the present invention on the signal transduction process in bacteria, the inhibiting effect of the compounds on the sporulation operon proteins Kinase A and Spo0F was examined. Specifically, the inhibition of autophosphorylation of Kinase A and the transphosphorylation of Spo0F was determined in the following assays. The Spo0F response regulator is the primary substrate for phosphorylation by the protein kinase, Kin A, involved in the sporulation process in bacteria. See D. Burbulys, K. A. Trach, J. A. Hoch, *Cell,* 64, 545–552 (1991). Spo0F and KinA were prepared from recombinant *E. coli* overexpressing the proteins (J. Cavanagh et al, *Amino Acids,* 6, 131–140 (1994) and references therein).

The following stock reagents were either prepared and used promptly or stored at the indicated temperature:

8×Salts: 2 M KCl (5 mL), 1 M $MgCl_2$ (800 mL), 1 M $CaCl_2$ (100 mL), 10 mg/mL phenylmethylsulfonyl fluoride (200 mL), 1 M dithioreitol (50 mL), 0.25 M $Na_2EDTA$ (32 mL) and $H_2O$ 3.82 mL (−20° C.)

5×Loading Dye: 0.5M TRIS-HCl, pH 6.8 (7.5 mL), 10% SDS (2 mL) 0.1% bromophenol blue (0.5 mL), 100% glycerol (3 mL) and 12.5 M 2-mercaptoethanol (0.3 mL)

1–1.3 mg/mL KinA: 15 mM TRIS-HCl, pH 8.0, 6 mM KCl; 4 mM 2-mercaptoethanol; 40% glycerol (−20° C.)

1 mg/mL Spo0F: 17.5 mM TRIS-HCl, pH 8.0; 0.7 mM KCl; 0.7 mM $MgCl_2$; 0.7 mM $CaCl_2$; 5 mM 2-mercaptoethanol; 30% glycerol (−20° C.)

5% Stacking Gel: 40% 29:1 acrylamide:bis acrylamide (1.25 mL), 0.5 M TRIS-HCl, pH 6.8 (2.5 mL), 10% SDS (0.1 mL), D-$H_2O$ (6.15 mL) 10% ammonium persulfate (100 mL) and TEMED (25 mL)

SDS Running Buffer: TRIS-BASE (3.02 g), glycine (14.4 g), SDS (1 g), D-$H_2O$ (to 1 L)

The reaction mixture was prepared from 8×Salts (87 μL), 1M TRIS, pH 8 (118 μL), 50% glycerol (63 μL), Spo0F (14.1 μL) and KinA (7.0 μL). Microcentrifuge tubes were charged with the reaction mixture (18.5 μL) and a 1.0 mM solution of the test compound in 5% DMSO (18.5 μL), and incubated for 15 min on ice. 100 mM ATP solution (3.0 μl, containing 625 μCi [$^{32}$P]ATP) was added, and the mixture left for 10 minutes at room temperature. The reaction was quenched with 5× loading dye (10 μL per tube) and the samples were loaded on a prepared 5% Stacking Gel, or stored on dry ice until ready for use. The prepared wells were filled with SDS Running Buffer, samples were loaded into the wells, and 80 volts were applied to the gel until the dye front reached the bottom of the stacking gel. The voltage was then increased to 250 volts until electrophoresis was complete. Radioactive bands in the gel corresponding to phosphorylated KinA and Spo0F were imaged and quantitated with a phosphoimager.

If either enzyme was inhibited (as evidenced by the absence of labelled protein in the developed gel), an $IC_{50}$ was calculated by running the assay with a range of inhibitor concentrations from 1 to 500 μM. After electrophoresis of the reaction mixtures, percent inhibition was determined by measuring the concentration of radioactive phosphorus with a phosphoimager and calculating the values using a software program (BioRad Molecular Analyst).

MIC Antimicrobial Assay

The in vitro antimicrobial activity of the compounds was determined by the microdilution broth method following the test method from the National Committee for Laboratory Standards (NCCLS). This method is described in the NCCLS Document M7-A2, Vol.10, No.8 "Methods for Dilution Antimicrobial Susceptibility Test for Bacteria that Grow Aerobically—Second Edition."

In this method two-fold serial dilutions of drug in cation supplemented Mueller-Hinton broth are added to wells in microdilution trays. The test organisms are prepared by adjusting the turbidity of actively growing broth cultures so that the final concentration of test organism after it is added to the wells is approximately $5 \times 10^4$ CFUs/well).

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray.

The antibacterial results demonstrated that the compounds according to the invention have a broad spectrum of activity against the bacterial strains tested including one or more of the following test organisms:

*S. aureus* (ATCC 29213)

Methicillin resistant *S. aureus* (oc 2089, 2878 and 667)

*E. faecalis* (oc 3041)

*E. faecium* (oc 2993)

*E coli* (oc 2530)

*S. epidermidis* (oc 2603)

*K. pneumoniae* (oc 1943)

*P. aeroginosa* (oc 161)

The compounds according to this invention which have good antimicrobial activity can be used in antimicrobial compositions, as antiseptics or disinfectants for local and general application, topically for prevention or treatment of skin lesions, and, where in vivo activity is present, for systemic treatment of bacterial infections in the form of conventional antimicrobial pharmaceutical compositions appropriate for the intended use.

As antiseptics for human or veterinary use, the concentration of active compound can vary from 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos or for the preparation of shower gels and foaming lotions. Foaming solutions containing the compounds according to the invention are obtained using amphoteric, anionic, cationic, or non-ionic surfactants at a concentration of 0.3 to 30%, humectants such as glycols and polyethylene glycols at a concentration of 0 to 20%, ethylene oxide and polypropylene copolymers at a concentration of 0 to 20%, and an alcohol (ethanol, isopropyl or benzyl alcohol) or a polyol, such as glycerol, at a concentration of 0 to 15%, as well as agents for complexing Ca++, Mg++ and heavy metal ions, salts for providing an appropriate buffer capacity, agents for imparting viscosity, natural, cellulosic or synthetic polymers, fragrances, preservatives and colorants.

If the compound according to the invention has a poor solubility in water, it is possible to use microemulsions, micellar solutions or similar surfactant systems which permit solubilization in water. These solutions can be used in diluted or undiluted form and can be dispensed by means of a vasopump or liquified or non-liquified propellants.

With the same constituents at appropriate concentrations, the compounds according to the invention can also be used to prepare simple aqueous solutions or sprays for making operative fields antiseptic, for postoperative treatments, for the treatment of burns, superinfected eczema, gluteal erythema, wounds or acne, or for deodorants. Alternatively, the compounds can be formulated in simple alcoholic solutions in the form of sprays containing 20 to 80% by weight of alcohol, optionally including excipients which make it possible to penetrate the keratinized layers of the skin and superficial body growths, such as Azone. These solutions can be used for making the skin antiseptic before puncture, for preparing the operative field, by nursing staff for making their hands antiseptic and for treating closed infected dermatosis, folliculitis, perionchyia and acne. Compositions for topical application may take the form of liquids, creams or gels, containing a therapeutically effective concentration of a compound of the invention admixed with a dermatologically acceptable carrier.

Moreover, the rapid lethal action on germs of the compounds of the invention enables them to be used as surface disinfectants at concentrations which can vary from 0.1 to 4% by weight. In this case, the product is used in preparations such as aqueous or nonaqueous foaming detergent solutions, sprays or nebulizers. Preparations of this type are particularly useful in the hospital or veterinary sectors or agrifoodstuff industries. These preparations can contain the same constituents as those used in the antiseptic formulations, although a wide variety of organic solvents may be added.

Finally, for those compounds which exhibit in vivo activity, the invention further provides a method of treating bacterial infections, or enhancing the activity of other antibacterial agents, in warm-blooded animals, which comprises administering to the animals a compound of the invention alone or in admixture with a diluent or in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

(Route A)

2-[4-(1,1-dimethylethyl)phenyl]-1H-Benzimidazole-5-carboximidamide (a) 3,4-Diaminobenzimidate To 500 mL of ethanol in an ice bath was bubbled HCl (g) until the ethanol was saturated with the gas. 3,4-Diaminobenzonitrile (40.0 g, 0.300 mol) was dissolved in 500 mL of $CH_2Cl_2$ and added to the cooled ethanol solution. HCl (g) was continued to be bubbled through the solution at 0° C. The reaction was sealed and warmed up to 25° C. The reaction was followed by TLC along with IR spectroscopy for the disappearance of the nitrile. Once there were no more evidence of the nitrile, the reaction mixture was put under vacuo to remove 75% of the solvents. Ether (500 mL) was added, the precipitate was filtered, washed with ether (3×250 mL), and dried under nitrogen. The 3,4-diaminobenzimidate was used to synthesize 3,4-diaminobenzamidine dihydrochloride without any further purification.

(b) 3,4-Diaminobenzamidine dihydrochloride

To 500 mL of ethanol at 25° C. was bubbled $NH_3$ (g) until the ethanol was saturated with the gas. The imidate was added and the mixture was heated to 80° C. under nitrogen for 4 h. The reaction was followed by TLC with 1:1 Hex/EtOAc. Once the reaction was over, the reaction solution was place under vacuo to remove all solvents. The residue was recrystallized from 2N HCl to afford 3,4-diaminobenzamidine dihydrochloride (51.4 g, 76%) as an off-white solid: $^1$H NMR (DMSO-$d_6$) δ9.14 (bs, 2 NH), 8.92 (bs, 2 NH), 7.59 (s, 1 arom-H), 7.51 (d, 1 arom-H, J=8 Hz), 6.95 (d, 1 arom-H, J=8 Hz).

2-[4-(1,1-dimethylethyl)phenyl]-1H-Benzimidazole-5-carboximidamide

To 4-tert-butylbenzaldehyde (0.4000 g, 0.00247 mol) was added 3 mL of 40% $NaHSO_3$ (aq). The mixture was stirred for 2 h at 25° C. 3,4-Diaminobenzamidine dihydrochloride (0.56 g, 0.0025 mol) and ethanol (8 mL) were added. The mixture was refluxed for 3 h. The reaction was then poured into water. The precipitate filtered and recrystallized from 2N HCl to afford 1H-benzimidzole-5-carboximidamide, 2-[4-(1,1-dimethylethyl)phenyl]- (400 mg, 44%) as a white solid: $^1$H NMR (DMSO-$d_6$) δ9.47 (bs, 2 NH), 9.15 (bs, 2 NH), 8.30 (d, 2 arom-H, J=8 Hz), 8.21 (s, 1 arom-H), 7.88 (d, 1 arom-H, J=8 Hz), 7.73 (d, 1 arom-H, J=9 Hz), 7.68 (d, 2 arom-H, J=8 Hz), 1.35 (s, 9 tert-butyl-H).

The following compounds are prepared using the procedure of Example 1 (Route A) and appropriate starting materials. The starting materials are commercially available or may be prepared in accordance with the following Reference Examples.

TABLE 7

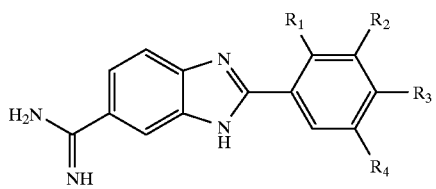

| Example | $R_1$ | $R_2$ | $R_3$ | $R_4$ | m.p. |
|---|---|---|---|---|---|
| 2 | H | H | Ph | H | 297–298 |
| 3 | H | H | $CF_3$ | H | 268–270 |
| 4 | H | H | i-Propyl | H | 282–283 |
| 5 | H | H | $N(Ph)_2$ | H | >300 |
| 6 | H | $OCH_2Ph$ | H | $OCH_2Ph$ | 195–197 |
| 7 | H | $CF_3$ | H | $CF_3$ | 199–201 |
| 8 | H | H | $C(CH_3)_2CH_2CH_3$ | H | 237–238 |
| 9 | H | t-Butyl | OH | t-Butyl | 286–287 |
| 10 | H | H | t-Butyl | H | 249–251 |
| 11 | H | H | $OCH_2(4-NO_2Ph)$ | H | 290–291 |
| 12 | H | $OC_{10}H_{21}$ | $OC_{10}H_{21}$ | H | 255–257 |
| 13 | H | H | CHCHPh | H | >300 |
| 14 | H | H | $N(C_4H_9)_2$ | H | 291–292 |
| 15 | H | H | $OCH_2Ph$ | H | 253–254 |
| 16 | H | $OCH_2Ph$ | $OCH_2Ph$ | H | 247–248 |
| 17 | H | H | F | H | >300 |
| 18 | H | I | OH | I | >300 |
| 19 | H | Cl | H | Cl | >300 |
| 20 | H | t-Butyl | H | t-Butyl | 270–275 |
| 21 | H | Ph | H | Ph | 204–206 |
| 22 | H | H | $NHCH_2Ph$ | H | 265–267 |
| 23 | H | H | OH | t-Butyl | 299–300 |
| 24 | H | H | Pyrrolinyl | H | >300 |
| 25 | H | H | $N(CH_2CH_2CN)_2$ | H | 284–286 |
| 26 | H | H | $N(CH_2Ph)_2$ | H | 271–273 |
| 27 | OH | H | H | H | >300 |
| 28 | $OCH_3$ | H | $OCH_3$ | Br | 254–255 |
| 29 | $OCH_3$ | t-Butyl | H | t-Butyl | >250 |
| 30 | OH | t-Butyl | H | t-Butyl | 272–273 |
| 31 | OH | I | H | I | 223–224 |
| 32 | OH | Br | H | Br | 262–263 |
| 33 | OH | $NO_2$ | H | $NO_2$ | >300 |
| 34 | OH | t-Butyl | H | H | 240–246 |
| 35 | OH | H | H | t-Butyl | >265 |
| 36 | OH | Cl | H | Cl | >300 |
| 37 | OH | Br | H | $OCH_3$ | 249–250 |
| 38 | OH | H | $N(CH_2CH_3)_2$ | H | >250 |
| 39 | OH | Ph | H | Ph | >300 |
| 40 | OH | Br | H | $NO_2$ | >300 |

TABLE 7-continued

| Example | R₁ | R₂ | R₃ | R₄ | m.p. |
|---|---|---|---|---|---|
| 41 | H | Pyridine | H | H | 230–236 |
| 42 | OCH₂COOH | t-Butyl | H | t-Butyl | >300 |
| 43 | H | H | 4-t-butyl-thiazol-2-yl | H | >300 |
| 44 | H | H | 9-oxofluoren-2-yl | H | >300 |
| 45 | H | H | 2,6-dinitro-4-trifluoromethylphenoxy | H | 237–238 |

TABLE 8

| Example | R | R₁ | R₂ | R₃ | R₄ | R₅ | m.p. |
|---|---|---|---|---|---|---|---|
| 46 | H | H | H | H | H | CH₃ | >245 |
| 47 | H | H | H | Amidine | H | H | 255–257 |
| 48 | H | H | H | H | H | H | 253 |
| 49 | H | NO₂ | H | Cl | H | H | 296–298 |
| 50 | H | H | H | NO₂ | H | H | 298–300 |
| 51 | H | H | H | NH₂ | H | H | >300 |
| 52 | H | H | H | COOEt | H | H | 261–262 |
| 53 | H | H | OCH₃ | OCH₃ | OCH₃ | H | 286–288 |
| 54 | H | H | H | OCH₃ | H | H | 269–270 |
| 55 | H | H | OCH₃ | H | OCH₃ | H | 236–238 |
| 56 | H | H | H | t-Butyl | H | H | 291–292 |
| 57 | H | H | NO₂ | NO₂ | H | H | 234–236 |
| 58 | H | H | NH₂ | NH₂ | H | H | 282–283 |
| 59 | H | H | H | Cl | H | H | >300 |
| 60 | H | H | Cl | Cl | H | H | >300 |
| 61 | NO₂ | H | H | H | H | H | 173–176 |
| 62 | NH₂ | H | H | H | H | H | 168–170 |

TABLE 9

| Example | R₁ | R₂ | R₃ | m.p. |
|---|---|---|---|---|
| 63 | H | H | H | 173–174 |
| 64 | CF₃ | H | H | 257–259 |
| 65 | H | CH₃ | H | >300 |
| 66 | Cl | H | Cl | 292–293 |
| 67 | Cl | Cl | H | 273–274 |
| 68 | H | t-Butyl | H | 265–266 |
| 69 | H | Cl | H | 294–296 |
| 70 | H | OCH₃ | H | 161–163 |

TABLE 10

| Example | R | m.p. |
|---|---|---|
| 71 | dibenzofuran-2-yl | >300 |
| 72 | fluoren-2-yl | >300 |
| 73 | 9-ethylcarbazol-2-yl | 297–298 |
| 74 | naphth-2-yl | >300 |
| 75 | 1-hydroxynaphth-2-yl | 297–298 |
| 76 | julolidin-yl | 291 |
| 77 | 9-hydroxyjulolidin-yl | |
| 78 | 1',3',3'-trimethylspiro[2H-chromene-2,2'-indoline]-yl | 196 |
TABLE 11
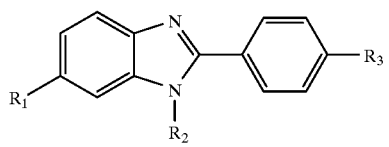
| Example | $R_1$ | $R_2$ | $R_3$ | m.p. |
|---|---|---|---|---|
| 79 | H | H | 4-amidinophenoxy | 213–215 |
| 80 | acetamidino | H | benzimidazol-5-yloxy | 245–248 |
| 81 | acetamidino | H | 4-phenylpiperazin-1-yl | >300 |

TABLE 11-continued

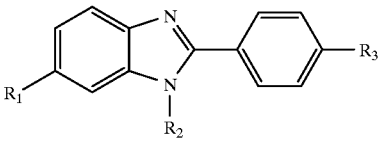

| Example | $R_1$ | $R_2$ | $R_3$ | m.p. |
|---|---|---|---|---|
| 82 |  | 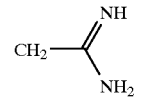 | N(Ph)$_2$ | 283–284 |

TABLE 12

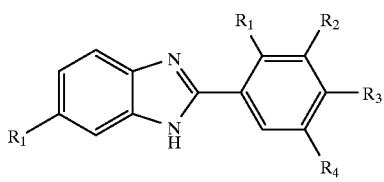

| Example | R | $R_1$ | $R_2$ | $R_3$ | $R_4$ | m.p. |
|---|---|---|---|---|---|---|
| 83 | 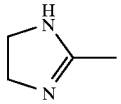 | H | H | OPh | H | 257–258 |
| 84 | 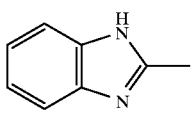 | H | H | OPh | H | >300 |
| 85 | 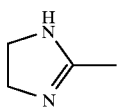 | OH | t-butyl | H | t-butyl | 275–276 |
| 86 | 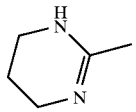 | OH | t-butyl | H | t-butyl | >300 |
| 87 | 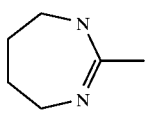 | OH | t-butyl | H | t-butyl | >300 |
| 88 | 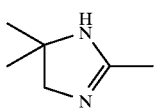 | OH | t-butyl | H | t-butyl | >260 |
| 89 | COOH | | OH | t-butyl | H | t-butyl | 217–219 |

EXAMPLE 93
Route B(i)
2-(4-Phenoxyphenyl)-1H-benzimidazole-5-carboximidamide
(a) 2-(4-phenoxyphenyl)-1H-Benzimidazole-5-nitrile To 4-phenoxybenzaldehyde (4.0 g, 0.020 mol) was added 20 mL of 40% NaHSO$_3$ (aq). The mixture was stirred for 2 h at 25° C. 3,4-Diaminobenzonitrile (3.36 g, 0.0252 mol) and ethanol (50 mL) were added. The mixture was refluxed for 4 h. The reaction was then poured into water. The precipitate was filtered and recrystallized from ethyl acetate to afford 3.6 g (57%) of 2-(4-phenoxyphenyl)-1H-benzimidazole-5-nitrile.

(b) Imidate

To 50 mL of ethanol in an ice bath was bubbled HCl(g) until the ethanol was saturated with the gas. 2-(4-phenoxyphenyl)-1H-benzimidazole-5-nitrile (0.50 g, 0.0016 mol) was dissolved in 50 mL of $CH_2Cl_2$ and added to the cooled ethanol solution. HCl (g) was continued to be bubbled through the solution at 0° C. The reaction was sealed and warmed up to 25° C. The reaction was followed by TLC along with IR spectroscopy for the disappearance of the nitrile. Once there were no more evidence of the nitrile, the reaction mixture was put under vac cuo to remove 75% of the solvents. Ether (50 mL) was added, the precipitate was filtered, washed with ether (3×50 mL), and dried under nitrogen. The product was used without any further purification to make the amidine dihydrochloride.

(c) 2-(4-phenoxyphenyl)-1H-benzimidazole-5-carboximidamide, dihydrochloride

To 100 mL of ethanol at 25° C. was bubbled $NH_3$ (g) until the ethanol was saturated with the gas. The imidate was added and the mixture was heated to 70° C. under nitrogen for 4 h. The reaction was followed by TLC with 1:1 Hex/EtOAc. Once the reaction was over, the reaction solution was place under vac cuo to remove all solvents. The residue was recrystallized from 2N HCl to afford the amidine 2-(4-phenoxyphenyl)-1H-benzimidazole-5-carboximidamide (350 mg, 54%) as a white solid: $^1$H NMR (DMSO-$d_6$) δ9.50 (bs, 2 NH), 9.18 (bs, 2 NH), 8.41 (d, 2 arom-H, J=9 Hz), 8.22 (s, 1arom-H), 7.89 (d, 1 arom-H, J=8 Hz), 7.80 (d, 1 arom-H, J=8 Hz), 7.51 (d, 1 arom-H, J=8 Hz), 7.48 (d, 1 arom-H, J=8 Hz), 7.18 (m, 5 arom-H).

EXAMPLE 94

Route B(ii)

2-(4-hydroxyphenyl)-1H-Benzimidazole-5-nitrile

To 50 mL of ethanol in an ice bath was bubbled HCl (g) until the ethanol was saturated with the gas. 4-Hydroxybenzonitrile (2.7 g, 0.023 mol) was dissolved in 50 mL of $CH_2Cl_2$ and added to the cooled ethanol solution. HCl (g) was continued to be bubbled through the solution at 0° C. The reaction was sealed and warmed up to 25° C. The reaction was followed by TLC along with IR spectroscopy for the disappearance of the nitrile. Once there were no more evidence of the nitrile, the reaction mixture was put under vac cuo to remove 75% of the solvents. Ether (50 mL) was added, the precipitate filtered, washed with ether (3×50 mL) and dried under nitrogen. The imidate was use to make 2-(4-hydroxyphenyl)-1H-benzimidazole-5-nitrile without any further purification.

A mixture of 3,4-diaminobenzonitrile (3.0 g, 0.023 mol) and the imidate in 500 mL of methanol was heated at 70° C. under nitrogen. The reaction was followed by TLC with 1:1 Hex/EtOAc. After 4 h the reaction solution was place under vac cuo to remove all solvents. The residue was recrystallized from ethyl acetate to afford 4.5 g (85%) of 2-(4-hydroxyphenyl)-1H-benzimidazole-5-nitrile.

EXAMPLE 95

5-(4,5-Dihydro-1H-imidazol-2-yl)-2-(4-phenoxyphenyl)-1H-Benzimidazole (a) 2-(4-phenoxyphenyl)-1H-Benzimidazole-5-carboxylic acid, methyl ester To 4-phenoxybenzaldehyde (3.0 g, 0.02 mol) was added 21 mL of 40% $NaHSO_3$ (aq). The mixture was stirred for 1 h at 25° C. Methyl-3,4-diaminobenzoate (2.5 g, 0.02 mol) and ethanol (15 mL) were added. The mixture was refluxed for 4 h. The reaction was then poured into water. The precipitate filtered and recrystallized from EtOAc to afford 2-(4-phenoxyphenyl)-1H-benzimidazole-5-carboxylic acid, methyl ester (5.06 g, 97%) as a white solid.

(b) 5-(4,5-dihydro-1H-imidazol-2-yl)-2-(4-phenoxyphenyl)-1H-benzimidazole

Ethylenediamine (0.70 g, 0.0116 mol) in benzene (10 mL) was added dropwise to a stirred solution of trimethyl aluminum (2.0M, 0.12 mol) such that the temperature does not exceed 10° C. At the end of methane evolution, the ester 2-(4-phenoxyphenyl)-1H-Benzimidazole-5-carboxylic acid, methyl ester (2.5 g, 0.00726 mol) was gradually added at 25° C. The reaction mixture was then refluxed for 3 h. The reaction was cooled and treated with 3 mL of $H_2O$, diluted with MeOH, 10 mL of $CH_2Cl_2$ and refluxed for 15 min. The mixture was filtered and washed with EtOAc to remove aluminum hydroxides. The filtrate was concentrated and the residue was recrystallized from 2N HCl to afford 5-(4,5-dihydro-1H-imidazol-2-yl)-2-(4-phenoxyphenyl)-1H-benzimidazole (2.3 g, 74%) as a white solid.

EXAMPLE 96

2-[5-(4.5-dihydro-4,4-dimethyl-1H-imidazol-2-yl)-1H-benzimidazol-2-yl}-3,5-bis(1,1-dimethylethyl)-phenol (a) 2-[3,5-bis(1,1-dimethylethyl)-2-hydroxyphenyl]-1H-Benzimidazole-5-carbonitrile To 3,5-di-tert-butylsalicylaldehyde (8.98 g, 0.0383 mol) was added 55 mL of 40% $NaHSO_3$ (aq). The mixture was stirred for 5 h at 25° C. 3,4-Diaminobenzonitrile (5.13 g, 0.0385 mol) and ethanol (300 mL) was added. The mixture was refluxed for 24 h. The reaction was then poured into water. The precipitate was filtered and recrystallized from $CH_2Cl_2$/Hexanes to afford 1H-benzimidazole-5-carbonitrile, 2-[3,5-bis(1,1-dimethylethyl)-2-hydroxyphenyl]- (10.86 g, 82%) as a white solid.

(b) Phenol, 2-[5-(4,5-dihydro-4,4-dimethyl-1H-imidazol-2-yl)-1H-benzimidazol-2-yl}-3,5-bis(1,1-dimethylethyl)-

To 60 mL of ethanol in an ice bath was bubbled HCl (g) until the ethanol was saturated with the gas. 1H-benzimidazole-5-carbonitrile, 2-[3,5-bis(1,1-dimethylethyl)-2-hydroxyphenyl]- (0.5236 g, 1.508 mmol) was added to the cooled ethanol solution. HCl (g) was continued to be bubbled through the solution at 0° C. The reaction was sealed and warmed up to 25° C. The reaction was followed by TLC along with IR spectroscopy for the disappearance of the nitrile. The reaction mixture was then put under vac cuo to remove 75% of the solvents. Ether (100 mL) was added and the precipitate was filtered, washed with ether (3×250 mL) and dried under nitrogen to yield the imidate. The imidate was used to make the amidine without any further purification.

To the imidate in MeOH (10 mL) was added 1,2-diamino-2-methylpropane (0.19 mL, 0.0018 mol). The mixture refluxed for 16 h under $N_2$. After cooling, the reaction solution was place under vac cuo to remove all solvents. The residue was recrystallized from 2N HCl to afford 0.400 g (63%) of phenol, 2-[5-(4,5-dihydro-4,4-dimethyl-1H-imidazol-2-yl)-1H-benzimidazol-2-yl}-3,5-bis(1,1-dimethylethyl)- as a white solid.

EXAMPLE 97

7-amino-2-[4-(diphenylamino)phenyl]-1H-benzimidazole-5-carboximidamide (a) 4-Amino-3,5-dinitrobenzonitrile To 4-chloro-3,5-dinitrobenzonitrile (9.8 g, 0.043 mol) in EtOAc (30 mL) and DMSO (20 mL) was added 1M ethanoic amonia (100 mL). The mixture was stirred for 1 h and filtered to afford the 4-amino-3,5-dinitrobenzonitrile (8.78 g, 98%) as a yellow solid.

(b) 3,4-Diamino-5-nitrobenzonitrile

To 4-amino-3,5-dinitrobenzonitrile (9.4 g, 0.045 mol) in EtOH (100 mL) was added $SnCl_2$ (30 g, 0.16 mol). The mixture was refluxed for 1 h. The reaction was then filtered and the filtrate concentrated to afford 3,4-diamino-5-nitrobenzonitrile (3.4 g, 42%) of an orange solid.

(c) 3,4-Diamino-5-nitrobenzimidate:

To 100 mL of ethanol in an ice bath was bubbled HCl (g) until the ethanol was saturated with the gas. 3,4-Diamino-5-nitrobenzonitrile (2.0 g, 0.011 mol) was dissolved in 20 mL of $CH_2Cl_2$ and added to the cooled ethanol solution. HCl (g) was continued to be bubbled through the solution at 0° C. The reaction was sealed and warmed up to 25° C. The reaction was followed by TLC along with IR spectroscopy for the disappearance of the nitrile. Once there were no more evidence of the nitrile, the reaction mixture was put under vac cuo to remove 75% of the solvents. Ether (100 mL) was added, the precipitate was filtered, washed with ether (3×50 mL), and dried under nitrogen. The 3,4-diaminobenzimidate was used to synthesize 3,4-diamino-5-nitrobenzamidine dihydrochloride without any further purification.

(d) 3,4-Diaminio-5-nitrobenzamidine dihydrochloride:

To 500 mL of ethanol at 25° C. was bubbled $NH_3$ (g) until the ethanol was saturated with the gas. The imidate was added and the mixture was heated to 80° C. under nitrogen for 4 h. The reaction was followed by TLC with 1:1 Hex/EtOAc. Once the reaction was over, the reaction solution was place under vac cuo to remove all solvents. The residue was recrystallized from 2N HCl to afford 3,4-diamino-5nitrobenzamidine dihydrochloride (1.86 g, 62%) as a rusty color solid.

(e) 7-nitro-2-[4-(diphenylamino)phenyl]-1H-Benzimidazole-5-carboximidamide

To 4-phenoxybenzaldehyde (430 mg, 2.17 mmol) was added 2 mL of 40% $NaHSO_3$ (aq). The mixture was stirred for 0.75 h at 25° C. 3,4-Diamino-5-nitrobenzonitrile dihydrochloride (402 mg, 1.50 mmol) and ethanol (5 mL) were added. The mixture was refluxed for 2.5 h. The reaction was then poured into water. The precipitate was filtered and recrystallized from ethyl acetate to afford (79 mg, 12%) of 1H-benzimidazole-5-carboximidamide, 7-nitro-2-[4-(diphenylamino)phenyl]- as a light yellow solid.

(f) 7-amino-2-[4-(diphenylamino)phenyl]-1H-Benzimidazole-5-carboximidamide

A mixture of 1H-benzimidazole-5-carboximidamide, 7-nitro2-[4-(diphenylamino)phenyl]- (50 mg, 0.11 mmol), catalytic amounts of 10% Pd/C and HCl (12N) in EtOH (20 mL) was placed in a parr reaction bottle under $H_2$ (50 psi) at 25° C. with shaking for 2 h. The reaction was then filtered over celite and the filtrate concentrated. The residue was recrystallized from 2N HCl/EtOH to afford 7-amino-2-[4-(diphenylamino)phenyl]-1H-benzimidazole-5-carboximidamide, (42 mg, 92%) as a white solid.

Reference Example 1

4-(4-Methoxyphenoxy)benzaldehyde

A mixture of 4-methoxyphenol (1.0 g, 0.00806 mol), 4-bromobenzaldehyde (1.49 g, 0.00805 mol), CuO (0.64 g, 0.00805 mol), potassium carbonate (1.11 g, 0.00803 mol) in pyridine (100 mL) was refluxed for 60 h. The reaction mixture was filtered into ice/water and the product was extracted with ethyl acetate. The organic layer was washed with water, dried ($MgSO_4$), concentrated and chromatographed with $CH_2Cl_2$ to afford 1.56 g (85%) of 4-(4-methoxyphenoxy)benzaldehyde.

Reference Example 2

2-[4-(4-cyanophenoxy)phenyl]1H-Benzimidazole-5-carbonitrile

A mixture of 1H-Benzimidazole-5-nitrile, 2-(4-hydroxyphenyl)- (2.6 g, 0.011 mol), potassium carbonate (4.0 g, 0.029 mol), and 4-fluorobenzonitrile (1.2 g, 0.0099 mol) in DMF (100 mL) was refluxed for 18 h. The mixture was then filtered (to remove the potassium carbonate) into an ice/water bath. The precipitate was collected and recrystallized from ethyl acetate to afford 0.7 g (21%) of 2-[4-(4-cyanophenoxy)phenyl]-1H-benzimidazole-5-carbonitrile.

Reference Example 3

4-(4-tert-Butylphenoxy)benzaldehyde

A mixture of 4-fluorobenzaldehyde (2.0 g, 0.0161 mol), 4-tert-butylphenol (2.42 g, 0.161 mol), and $K_2CO_3$ (9.0 g, 0.065 mol) in DMF (50 mL) was heated at 80° C. After 6 h, the reaction mixture was filtered into ice/water and the product was extracted with ethyl acetate. The organic layer was washed with water, dried ($MgSO_4$), concentrated and chromatographed with 1:1 hexane/ethyl acetate to give 3.9 g (95%) of 4-(4-tert-butylphenoxy)benzaldehyde.

Reference Example 4

4-(4-Phenyl-1-piperazinyl)-benzaldehyde

A solution of 4-flurobenzaldehyde (0.86 mL, 8.06 mmol), 1-phenylpiperazine (4.89 mL, 32 mmol), and potassium carbonate (1.10 g, 8.06 mmol) in acetonitrile was warmed to reflux under $N_2$. After 60 h, the reaction mixture was allowed to cool to 25° C., diluted with ethyl acetate (50 mL), washed with water (2×100 mL), filtered through a plug of silica, and was concentrated in vacuo to afford a yellow residue. The residue was washed with warm methanol, and dried under vacuum to afford benzaldehyde, 4-(4-phenyl-1-piperazinyl)- (1.71 g, 79%) was a white solid: $^1$H NMR ($CDCl_3$) δ9.82 (s, 1H), 7.90 (d, J=8.8 Hz, 2H), 7.33–7.20 (m, 3H), 7.01–6.80 (m, 4H), 3.38–3.28 (m, 4H), 3.20–3.13 (m, 4H).

solid: $^1$H NMR($CDCl_3$) δ9.78 (s, 1H), 8.54 (s, 1H), 7.89 (d, J=7.4 Hz, 1H), 6.83 (d, J=7.4 Hz, 1H), 3.75 (m, 4H), 1.80–1.65 (m, 6H).

Reference Example 5

3-tert-Butyl-2-hydroxybenzaldehyde

A mixture of 2-tert-butylphenol (15 g, 0.010 mol), powdered NaOH (20 g,0.50 mol), $H_2O$ (3.6 ml), and $CHCl_3$ (100 mL) was heated at 50° C. for 1 h. Then more powdered NaOH (12 g, 0.30 mol) was added at an increment of 2 g every 15 min. At the end of the NaOH additions, the reaction was continued to be heated at 56° C. for 1 h. After cooling, the reaction was acidified with HCl (12N). The chloroform fraction was separated, dried ($MgSO_4$), and concentrated. The residue was loaded on a silica gel column eluted with $CH_2Cl_2$ to give 3-tert-butyl-2-hydroxybenzaldehyde (4.6 g, 26%) as a solid.

Reference Example 6

2-(tert-Butylhydroxyacetate)-3,5-di-tert-butylbenzaldehyde

A solution of 3,5-di-tert-butyl-2-hydroxybenzaldehyde (1 g, 4.27 mmol) and sodium hydride (144 mg, 6.0 mmol) in dimethylformamide (50 mL) at 25° C. under $N_2$ was treated with tert-butyl bromoacetate (0.75 mL, 4.7 mmol) via syringe. After 8 h, the reaction mixture diluted with ethyl acetate (50 mL), washed with water (2×25 mL), filtered through a plug of silica and was concentrated in vacuo to afford 2-(tert-butyl hydroxyacetate)-3,5-di-tert-butylbenzaldehyde (1.48 g, 100%) as a yellow residue that was used without further purification: $^1$H NMR(CDCl$_3$) δ10.35 (s, 1H), 7.65 (d, J=3.2 Hz, 1H), 7.62 (d, J=3.2 Hz, 1H), 4.42 (s, 1H), 1.56 (s, 9H), 1.45 (s, 9), 1.37 (s, 9H).

Reference Example 13

3,5-Diphenylbenzaldehyde

A solution of 3,5-diphenylbenzoic acid (1 g, 3.65 mmol) in tetrahydrofuran (50 mL) was treated with a solution of lithium aluminum hydride (2.6 mL, 1M, 2.6 mmol) in tetrahydrofuran at 25° C. under $N_2$. After 3 h, the reaction mixture was carefully treated with satd. aqueous ammonium chloride (1 mL), diluted with ethyl acetate (50 mL), washed with satd. aqueous ammonium chloride (2×50 mL), dried (MgSO$_4$), and was concentrated in vacuo to afford a white solid that was used without any further purification. This solid residue was diluted with ethyl ether (20 mL) was treated with manganese dioxide (6.6 g, 76.7 mmol) at 25° C. After 12 h, the reaction mixture was filtered through a plug of celite, and was concentrated in vacuo. Purification by flash chromatography afforded 2 (410 mg, 43%) as a solid: $^1$H NMR(CDCl$_3$) δ10.23 (s, 1H), 8.25–8.20 (m, 5H), 8.14 (s, 2H), 7.66–7.45 (m, 6H).

We claim:

1. A compound having antimicrobial activity selected from those of the Formula I:

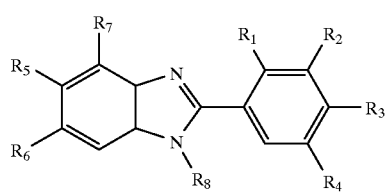

Formula I wherein:

$R_1$ is selected from H, OH, and $(C_1-C_6)$alkoxy;

$R_2$, $R_3$ and $R_4$ are independently selected from H, OH, branched or unbranched $(C_1-C_{10})$alkyl, $(C_1-C_{10})$alkoxy, —O$(C_1-C_6)$alkylphenyl, —OCH$_2$(4-NO$_2$phenyl), CF$_3$, halo, phenyl, substituted phenyl; wherein the substituents are selected from halogen, $(C_1-C_6)$alkoxy, nitro, NH$_2$, and $(C_1-C_6)$alkyl; —$(C_1-C_6)$alkylphenyl, nitro, —O(CH$_2$)$_q$N(($C_1-C_6$) alkyl)$_2$ wherein q is 1–3, —NR$_{17}$R$_{18}$, —CH=CH-phenyl, and a moiety of the formula:

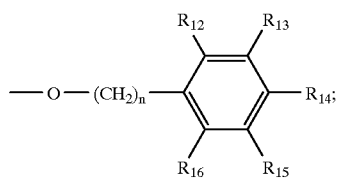

wherein n is an integer from 0–2;

$R_{12}$, $R_{13}$, $R_{14}$, $R_{15}$ and $R_{16}$ are independently selected from H, nitro, halo, CF$_3$, $(C_1-C_6)$ alkyl, $(C_1-C_6)$ alkoxy, and amino, sulfonate, —C(O)O$(C_1-C_6)$alkyl, and carboxyl;

$R_{17}$ and $R_{18}$ are independently selected from H, benzyl, phenyl, $(C_1-C_6)$alkyl, CH$_2$CN, and CH$_2$CH$_2$CN;

or $R_2$ and $R_3$ or $R_3$ and $R_4$ taken together with the phenyl ring to which they are attached form a moiety selected from those of the formulae:

$R_{20}$ is selected from $(C_1-C_3)$alkyl and OH;
$R_5$ is selected from H, amino and amidino;
$R_6$ is selected from moieties of the formula:

and

≡N, wherein:

$R_9$ and $R_{10}$ are H;
$R_7$ is selected from H, amino and nitro;
$R_8$ is selected from H and methyl;
and the pharmaceutically acceptable salts and esters thereof.

2. A compound having antimicrobial activity according to claim 1 wherein:

$R_1$ is selected from H, OH, $(C_1-C_6)$alkoxy;

$R_2$ is selected from H, branched or unbranched $(C_1-C_{10})$ alkyl), $(C_1-C_{10})$alkoxy, —O$(C_1-C_{10})$alkylphenyl, CF$_3$, halo, phenyl, nitro, and a moiety of the formula:

$R_3$ is selected from H, OH, branched or unbranched $(C_1-C_{10})$alkyl, $(C_1-C_{10})$alkoxy, —O$(C_1-C_6)$ alkylphenyl, —OCH$_2$(4-NO$_2$phenyl), CF$_3$, halo, phenyl, substituted phenyl; wherein the substituents are selected from halogen, $(C_1-C_6)$alkoxy, nitro, $NH_2$, and $(C_1-C_6)$alkyl; —$(C_1-C_6)$alkylphenyl, nitro, —$O(CH_2)_qN((C_1-C_6)alkyl)_2$ wherein q is 1–3, —$NR_{17}R_{18}$, —CH=CH-phenyl, and a moiety of the formula:

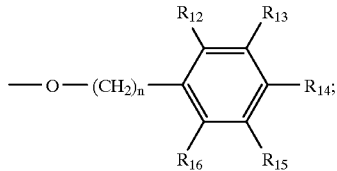

wherein $R_{17}$ and $R_{18}$ are independently selected from H, benzyl, phenyl, $(C_1-C_6)$alkyl, $CH_2CN$, $CH_2CH_2CN$;

$R_4$ is selected from H, branched or unbranched $(C_1-C_{10})$ alkyl, $(C_1-C_{10})$alkoxy; —$O(C_1-C_6)$alkylphenyl, $CF_3$, halo, phenyl, nitro and a moiety of the formula:

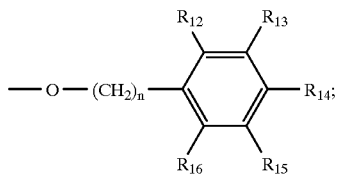

or $R_2$ and $R_3$ or $R_3$ and $R_4$ taken together with the phenyl ring to which they are attached form a moiety selected from those of the formulae:

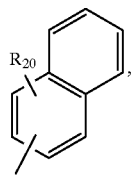

$R_{20}$ is selected from $(C_1-C_3)$alkyl and OH;
$R_5$ is selected from H, amino and amidino;
$R_6$ is selected from moieties of the formula:

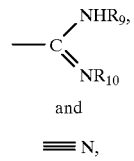

and

≡N, wherein:
$R_9$ and $R_{10}$ are H;
$R_7$ is selected from H, amino and nitro;
$R_8$ is selected from H and methyl;
$R_{12}$ is selected from H and nitro;
$R_{13}$ is selected from H, nitro, halo, $CF_3$, $(C_1-C_6)$ alkyl, $(C_1-C_6)$ alkoxy, and amino;
$R_{14}$ is selected from H, nitro, halo, $CF_3$, $(C_1-C_6)$ alkyl, $(C_1-C_6)$ alkoxy, amino, sulfonate, —$C(O)O(C_1-C_6)$ alkyl, and carboxyl;
$R_{15}$ is selected from H, nitro, halo, $CF_3$, $(C_1-C_6)$ alkyl, $(C_1-C_6)$ alkoxy, and amino;

$R_{16}$ is selected from H and nitro;
n is an integer from 0–2;
and the pharmaceutically acceptable salts and esters thereof.

3. A compound having antimicrobial activity according to claim 2 wherein:
$R_1-R_4$ are as described in claim 2;
$R_5$ is H;
$R_6$ is a moiety of the formula:

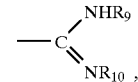

wherein:
$R_9$ and $R_{10}$ are H;
$R_7$, and $R_8$ are hydrogen and $R_{12}$ to $R_{16}$ are as described above in claim 2;
and the pharmaceutically acceptable salts and esters thereof.

4. A compound having antimicrobial activity selected from those of the formula

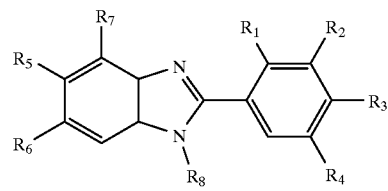

wherein:
$R_1$ is selected from H, OH, and $(C_1-C_6)$alkoxy;
$R_2$ is selected from H, branched or unbranched $(C_1-C_{10})$ alkyl, $(C_1-C_6)$alkoxy; —$O(C_1-C_{10})$alkylphenyl, $CF_3$, halo, phenyl, nitro and a moiety of the formula:

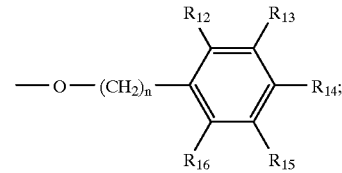

$R_3$ is selected from H, OH, branched or unbranched $(C_1-C_{10})$alkyl, $(C_1-C_{10})$alkoxy, —$O(C_1-C_6)$ alkylphenyl, $CF_3$, halo, phenyl, substituted phenyl; wherein the substituents are selected from halogen, $(C_1-C_6)$alkoxy, nitro, $NH_2$, and $(C_1-C_6)$alkyl; —$(C_1-C_6)$alkylphenyl and and a moiety of the formula:

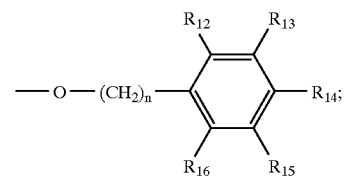

$R_4$ is selected from H, branched or unbranched $(C_1-C_{10})$ alkyl, and —$OCH_2$phenyl;
$R_5$ is H;

$R_6$ is amidine;

$R_7$ is H;

$R_8$ is H;

n is 0;

$R_{12}$ is H;

$R_{13}$ is selected from H, nitro, halo, $CF_3$, $(C_1-C_6)$ alkyl, $(C_1-C_6)$ alkoxy, and amino;

$R_{14}$ is selected from H, nitro, halo, $CF_3$, $(C_1-C_6)$ alkyl, $(C_1-C_6)$ alkoxy and amino;

$R_{15}$ is selected from H and $(C_1-C_6)$ alkoxy, and amino;

$R_{16}$ is H;

and the pharmaceutically acceptable salts and esters thereof.

5. The compound of claim 1 wherein $R_1-R_2$ are hydrogen, $R_3$ is phenyl, $R_4-R_5$ are hydrogen, $R_6$ is amidine, and $R_7$, and $R_8$ are all hydrogen.

6. The compound of claim 1 wherein $R_1-R_2$ are hydrogen, $R_3$ is —N(phenyl)$_2$, $R_4-R_5$ are hydrogen, $R_6$ is amidine, and $R_7$ and $R_8$ are all hydrogen.

7. The compound of claim 1 wherein $R_1-R_2$ are hydrogen, $R_3$ is —OCH$_2$phenyl, $R_4-R_5$ are hydrogen, $R_6$ is amidine, and $R_7$ and $R_8$ are all hydrogen.

8. The compound of claim 1 wherein $R_1$ is hydroxy, $R_2$ is t-butyl, $R_3$ is hydrogen, $R_4$ is t-butyl, $R_5$ is hydrogen, $R_6$ is amidine, and $R_7$ and $R_8$ are all hydrogen.

9. The compound of claim 1 wherein $R_1$ is hydroxy, $R_2$ is t-butyl, $R_3$ is hydrogen, $R_4$ is hydrogen, $R_5$ is hydrogen, $R_6$ is amidine, and $R_7$ and $R_8$ are all hydrogen.

10. The compound of claim 1 wherein $R_1-R_2$ are hydrogen; $R_3$ is a moiety of the formula:

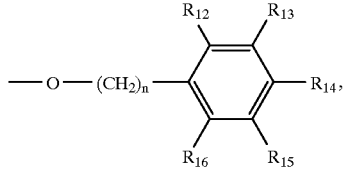

wherein n is 0, $R_{12}$ and $R_{13}$ are hydrogen, $R_{14}$ is hydrogen and $R_{15}$ and $R_{16}$ are hydrogen;

$R_4-R_5$ are hydrogen; $R_6$ is amidine; and $R_7$ and $R_8$ are all hydrogen.

11. The compound of claim 1 wherein $R_1-R_2$ are hydrogen; $R_3$ is a moiety of the formula:

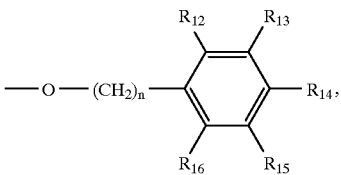

wherein n is 0, $R_{12}$ and $R_{13}$ are hydrogen, $R_{14}$ is —OCH$_3$ and $R_{15}$ and $R_{16}$ are hydrogen;

$R_4-R_5$ are hydrogen; $R_6$ is amidine; and $R_7$ and $R_8$ are all hydrogen.

12. The compound of claim 1 wherein $R_1-R_2$ are hydrogen; $R_3$ is a moiety of the formula:

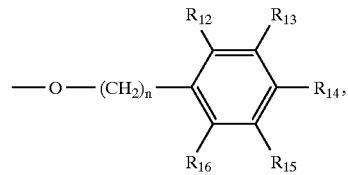

wherein n is 0, $R_{12}$ and $R_{13}$ are hydrogen, $R_{14}$ is chloro and $R_{15}$ and $R_{16}$ are hydrogen;

$R_4-R_5$ are hydrogen; $R_6$ is amidine; and $R_7$ and $R_8$ are all hydrogen.

13. The compound of claim 1 wherein $R_1$ is hydrogen; $R_2$ is a moiety of the formula:

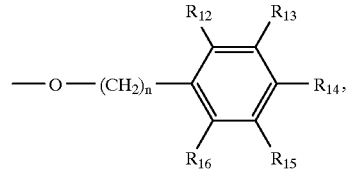

wherein n is 0, $R_{12}$ is hydrogen, $R_{13}$ is $CF_3$, and $R_{14}$, $R_{15}$ and $R_{16}$ are hydrogen;

$R_4-R_5$ are hydrogen; $R_6$ is amidine; and $R_7$ and $R_8$ are all hydrogen.

14. A pharmaceutical composition for treating bacterial infections comprising an effective amount of a compound selected from claim 1 in association with a pharmaceutically acceptable carrier.

15. A method of treating bacterial infections in mammals by administering to a mammal suffering from such infection a therapeutically effective amount of a compound selected from claim 1.

* * * * *